(12) United States Patent
Shambat et al.

(10) Patent No.: US 9,310,352 B2
(45) Date of Patent: Apr. 12, 2016

(54) BIOLOGICAL CELL NANOCAVITY PROBES

(71) Applicant: The Board of Trustees of the Leland Stanford Junior University, Palo Alto, CA (US)

(72) Inventors: Gary Shambat, San Francisco, CA (US); Jelena Vuckovic, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 14/107,797

(22) Filed: Dec. 16, 2013

(65) Prior Publication Data

US 2014/0170695 A1 Jun. 19, 2014

Related U.S. Application Data

(60) Provisional application No. 61/737,358, filed on Dec. 14, 2012.

(51) Int. Cl.
| | |
|---|---|
| *G02B 6/00* | (2006.01) |
| *G01N 33/50* | (2006.01) |
| *B29D 11/00* | (2006.01) |
| *G01N 21/77* | (2006.01) |
| *G01N 15/14* | (2006.01) |
| *G02B 6/26* | (2006.01) |
| *G01N 15/10* | (2006.01) |

(52) U.S. Cl.
CPC ...... *G01N 33/5005* (2013.01); *B29D 11/00721* (2013.01); *G01N 15/1434* (2013.01); *G01N 15/1456* (2013.01); *G01N 21/774* (2013.01); *G01N 21/7746* (2013.01); *G01N 2015/1006* (2013.01); *G01N 2021/7786* (2013.01); *G02B 6/262* (2013.01)

(58) Field of Classification Search
CPC ............... G01N 21/7703; G01N 33/54373; G01N 21/648; B82Y 20/00; G01L 1/246; G02B 6/00
USPC ............... 385/12, 15, 27, 30, 39, 43, 123
See application file for complete search history.

(56) References Cited

U.S. PATENT DOCUMENTS

| | | | |
|---|---|---|---|
| 7,348,181 | B2 | 3/2008 | Walt et al. |
| 8,377,699 | B2 | 2/2013 | Martins et al. |
| 2009/0118800 | A1 | 5/2009 | Deisseroth et al. |
| 2009/0326385 | A1 | 12/2009 | Hendriks et al. |
| 2013/0085398 | A1 | 4/2013 | Roukes |
| 2014/0130214 | A1* | 5/2014 | Solgaard et al. ......... 850/40 |

\* cited by examiner

*Primary Examiner* — Jennifer Doan
(74) *Attorney, Agent, or Firm* — Lumen Patent Firm

(57) ABSTRACT

An optical fiber is combined with a photonic crystal structure (PCS) that is optically coupled to the optical fiber. The fiber has an exposed fiber surface, and the PCS is affixed to the optical fiber and disposed on or in proximity to the exposed fiber surface. The PCS includes an elongate probe member configured for biological probing. The elongate probe member includes an optical resonant cavity. In an experiment, this was accomplished using an optical fiber tip with a semiconductor template attached to its side face. The semiconductor structure had a thin, needle-like tip (including a nanobeam cavity) which can be suitably inserted inside (or broken off inside) a biological cell without causing cytotoxicity.

10 Claims, 15 Drawing Sheets

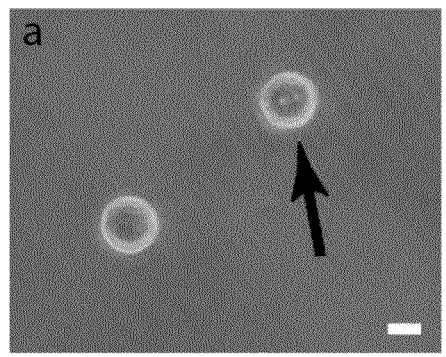 
FIG. 3A  FIG. 3B
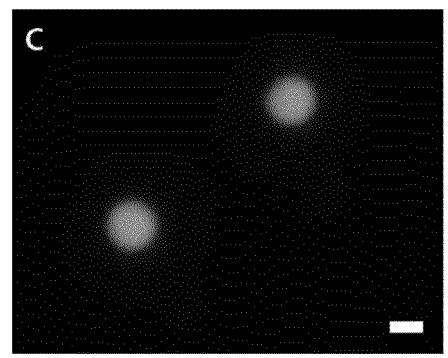 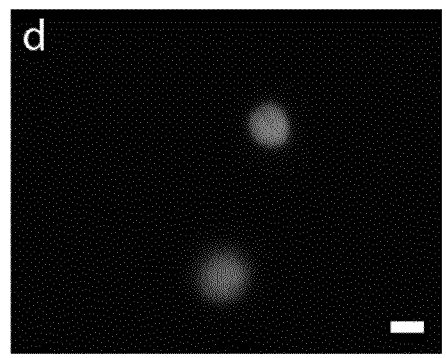
FIG. 3C  FIG. 3D

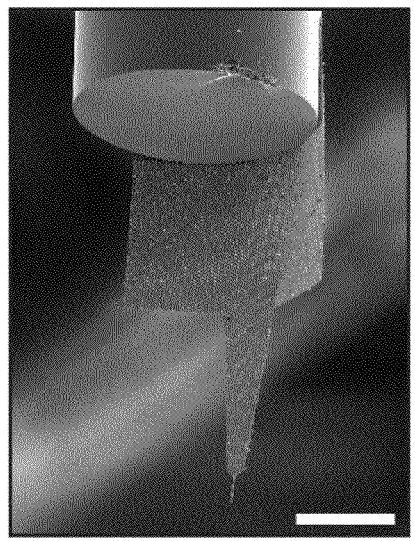
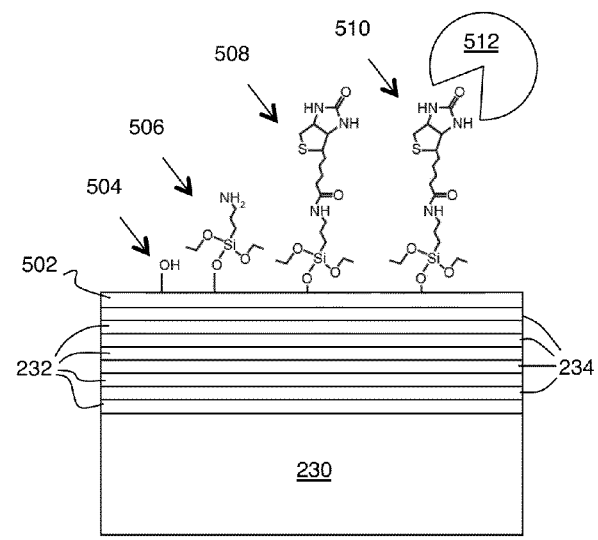
FIG. 5A
FIG. 5B
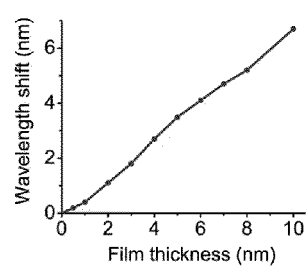
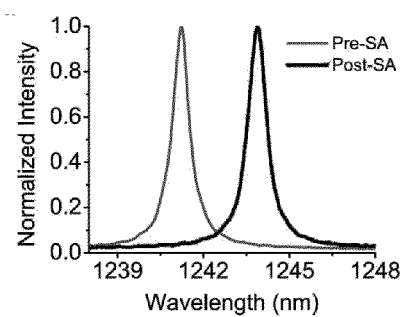
FIG. 5C
FIG. 5D

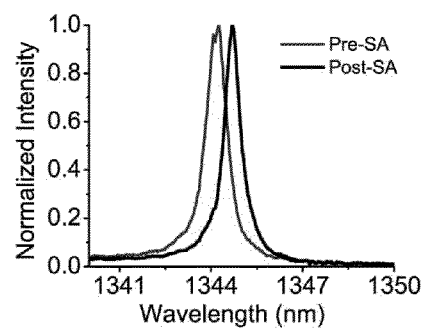
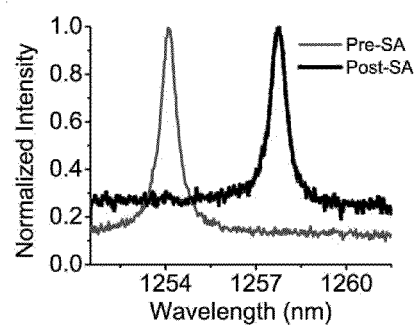
FIG. 5E    FIG. 5F
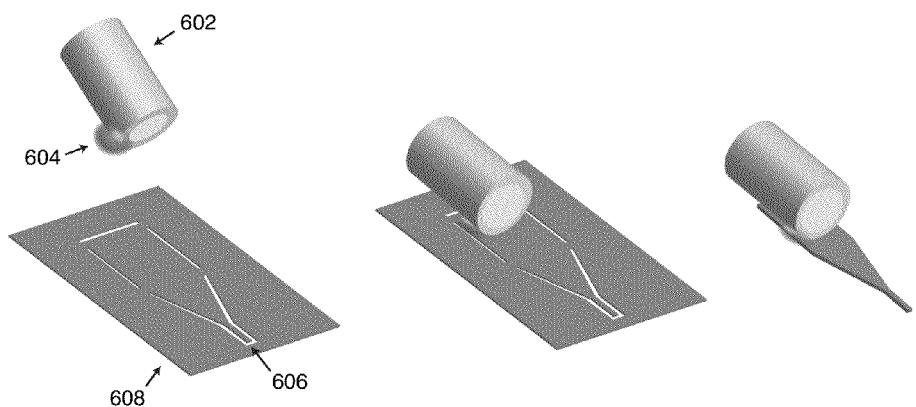
FIG. 6A    FIG. 6B    FIG. 6C

BIOLOGICAL CELL NANOCAVITY PROBES

CROSS REFERENCE TO RELATED APPLICATIONS

This application claims the benefit of U.S. provisional patent application 61/737,358, filed on Dec. 14, 2012, and hereby incorporated by reference in its entirety.

FIELD OF THE INVENTION

This invention relates to biological probing.

BACKGROUND

Nanoprobes of all kinds have been investigated for penetrating single cells in various studies. These include semiconductor nanowires, tapered optical fibers, carbon nanotubes, and other variant structures. These devices have opened the door to single cell studies but have tended to lack any significant optical functionality on the part of the device probe itself. The former devices have mainly served the purpose of shuttling biological material in and out of cells and have also been used to simply illuminate or collect light inside the cell.

US 2013/0085398 is a representative example, where 3-D arrays of optical emitters or optical detectors are inserted into tissue. However, various practical problems need to be overcome in order to make such approaches practical.

SUMMARY

This work is based on combining an optical fiber with a photonic crystal structure (PCS) that is optically coupled to the optical fiber. The fiber has an exposed fiber surface, and the PCS is affixed to the optical fiber and disposed on or in proximity to the exposed fiber surface. The PCS includes an elongate probe member configured for biological probing. The elongate probe member includes an optical resonant cavity. This cavity can be a dielectric or semiconductor nanocavity. This can provide numerous advanced photonic devices that can be used for intracellular sensing and control.

With the present tool, a sophisticated photonic cavity can now be placed wholly inside biological cells. In an experiment, this was accomplished by engineering a compound optical structure of an optical fiber tip with a specific semiconductor template attached to its side face. The semiconductor structure has a specific shape that allows for a thin, needle-like tip which can be suitably inserted inside a biological cell without causing cytotoxicity. In addition, the device was engineered to provide optical readout of the cavity.

An exemplary embodiment is an optical tool having a semiconductor photonic crystal cavity affixed to the tip of an optical fiber. The photonic crystal cavity is shaped like a needle and is thin enough to puncture individual biological cells without causing damage to the cell. The optical properties of the cavities remain intact even when placed inside the cells and can be used for numerous applications, e.g. the readout of the refractive index environment of the cell. Furthermore, these small cavities can be completely loaded in the cell by breaking them off the fiber tip.

Practice of the invention does not depend critically on how the PCS is optically coupled to the fiber. Possibilities include end face coupling (flat fiber end face or tapered fiber tip) and grating coupling. Accordingly, the exposed fiber surface (at which optical coupling occurs) can be a fiber end face, a tip of a tapered fiber, or a fiber grating coupler.

Preferably, the PCS includes a protective coating to protect it from degradation in operation as a biological probe. As described in greater detail below, such a protective coating can be a multi-layer structure of oxides. By making the PCS conform to a curved side surface of the fiber, its structural rigidity can be improved. This is helpful in cases where multiple probe insertions and retractions are to be done, and it is desired to prevent the probe from becoming folded against the fiber tip (e.g., as can be caused by surface tension forces).

Probing can be of any biological specimen, such as tissue, extra-cellular probing and intra-cellular probing of single cells. The probe can be either passive (i.e., no active element coupled to the optical resonant cavity) or active (one or more active elements are coupled to the resonant optical cavity). If present, suitable active elements include but are not limited to: quantum wells, quantum wires, quantum dots, emitters, detectors, near-field sensors, near-field emitters, photoacoustic elements, and nonlinear optical elements.

Such probes can be made by various methods. One approach is to first provide the PCS as a template connected to a surrounding membrane by two or more tabs. Next, the PCS is affixed to the optical fiber while the PCS is connected to the surrounding membrane by the tabs. Finally, breaking the tabs releases the PCS from the surrounding membrane. Another approach is to fabricate the PCS directly onto the fiber. Any approach that can provide the PCS suitably affixed to and optically coupled to the optical fiber can be employed.

Such probes can also be used in various ways. In addition to simply probing a biological target with the elongate probe member, it is possible to break the PCS such that part or all of the elongate probe member remains within the biological target.

Applications include, but are not limited to:
1) Label-free single-cell biological sensors for proteins, DNA, RNA, or small molecules.
2) Lasers (e.g., semiconductor lasers) inserted completely inside single biological cells.
3) Refractive index or near-field sensors of various fluids, organelles, or compartments of cells.
4) Optical traps inside single cells.
5) Ultrasmall and ultrasensitive photoacoustic probes in or near biological cells.
6) Near-field point source of illumination device.
7) Fiber-coupled nonlinear optics element.

Significant advantages can be realized. Device optical properties inside such biological material remain of high quality and therefore the numerous applications of photonic cavities can be translated into single-cell studies. Devices are shown to induce minimal harm to biological cells and can therefore be used for in vitro or in vivo studies for any number of biological or medical applications.

Variations include:
1) The technique is not limited to the particular photonic crystal cavity design employed, nor the exact membrane pattern, but applies to all photonic crystal cavity design variations.
2) The technique is not exclusive to photonic crystal cavities and can be used for any application where a nano- or microcavity is inserted into a cell.
3) The cavity need not bind to an optical fiber but can be connected to any handle or be freely inserted into a cell.
4) The optical pumping and collection scheme is not limited to the type employed here but variations on the optical tools can be performed.
5) The materials used are not limited to gallium arsenide but apply to any cavity-based material with or without active emitters.

6) The device is not limited to operation inside a single biological cell but can also be used in extracellular biological environments (in vivo or in vitro) including biological tissue, fluids, inside capillaries or blood vessels, or the human body.

BRIEF DESCRIPTION OF THE DRAWINGS

FIGS. 3A-D show short term cell viability results.

FIGS. 5A-F show nanoprobe detection of Streptavidin binding.

FIGS. 6A-C show an exemplary illustration of device assembly.

DETAILED DESCRIPTION

Here section A relates to an experimental demonstration of the above-described principles. Section B provides supplemental information relating to the experiments of section A.

A) Experimental Demonstration

A1) Introduction

Optical nanocavities are dielectric or hybrid metal-dielectric structures made from various semiconductors that can confine light to sub-wavelength spot sizes and produce intense local fields. These characteristics have been exploited in traditional fields of photonics in areas as diverse as optical interconnects, non-linear optics, cavity quantum electro-dynamics, and optomechanics. As a label-free biosensing element, photonic nanocavities can have incredibly low limits of detection due to their high quality (Q) factors. Nevertheless, realizing these extensive properties in a platform beyond the chip or wafer scale is challenging because devices are fabricated with standard top-down semiconductor processing, leaving cavities bound to parent substrates. A method to extract these nanocavities in a way that allows for facile insertion into single biological cells would open the door to a great number of novel studies merging the strengths of photonics with biology. Example applications could include real-time label-free sensing of proteins, DNA, mRNA, or μRNA, photoacoustic sensing at the single-cell level, near-field optical trapping of biomolecules, and nanolasers completely engulfed by single cells.

Previously we have demonstrated an epoxy-based technique to transfer large semiconductor templates of active material to the tips of optical fibers. Our nanocavity of choice in the past was the two-dimensional planar photonic crystal cavity since these devices can be incorporated in a thin membrane that is suitable for attachment to a fiber facet. The design provided both a stable mechanical handle for the nanocavities—which can then be used in remote environments—as well as a method to couple the cavity light to a fiber optic network. Moreover, cavities that were transferred and outside their original substrate environment still exhibited high Q modes and wavelength-scale mode volumes.

Here, by changing our device design to incorporate a "bayonet-like" semiconductor template that tapers down into a nanobeam photonic crystal cavity, we are able to create a new tool for probing single biological cells. Nanobeam cavities are one-dimensional cousins to traditional planar PC cavities and have only recently emerged as competitive alternatives. Aside from vertically grown micropost cavities (which pose a more challenging device construction), nanobeam cavities are the only dielectric cavity design that has the necessary sub-micron cross-section dimensions to penetrate cell membranes. In fact, our nanobeams are quite similar in size to well characterized nanowires and as we show, are minimally cytotoxic to cells while still providing the advanced functionality of engineered photonic probes.

A2) Results and Discussion

Figure 1A:
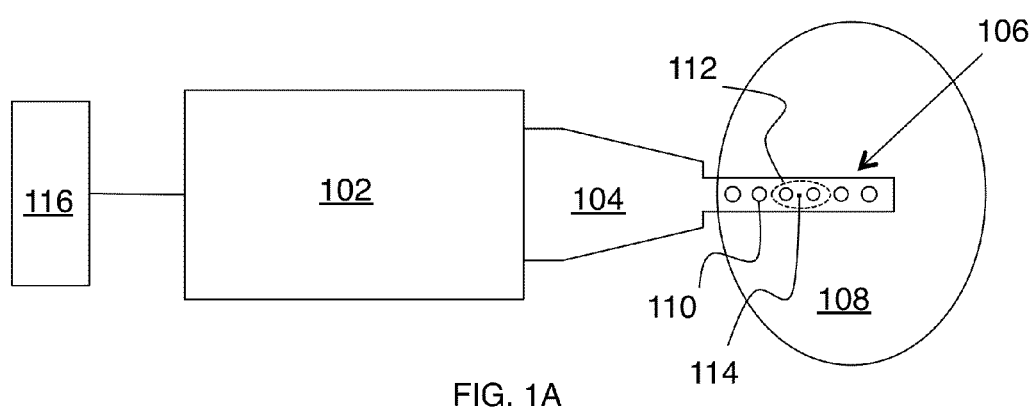
FIGS. 1A-F show photonic nanoprobe design and single cell interrogation.

FIGS. 1A-F show photonic nanoprobe designs and single cell interrogation. FIG. 1A is a schematic of photonic crystal nanobeam probe for single-cell investigation. Here the nanobeam cavity 106 extends from a larger semiconductor template 104 which is mounted on the side edge of a multimode optical fiber 102 that is connected to a detector 116. Nanobeam cavity 106 penetrates a cell 108 to provide sensing modalities such as label-free protein or DNA/RNA detection. The cavity mode is schematically depicted with dashed lines (112), and can be defined by photonic crystal features (one of which is referenced as 110). Optionally, an active element 114 can be disposed in the photonic cavity.

Figure 1B:
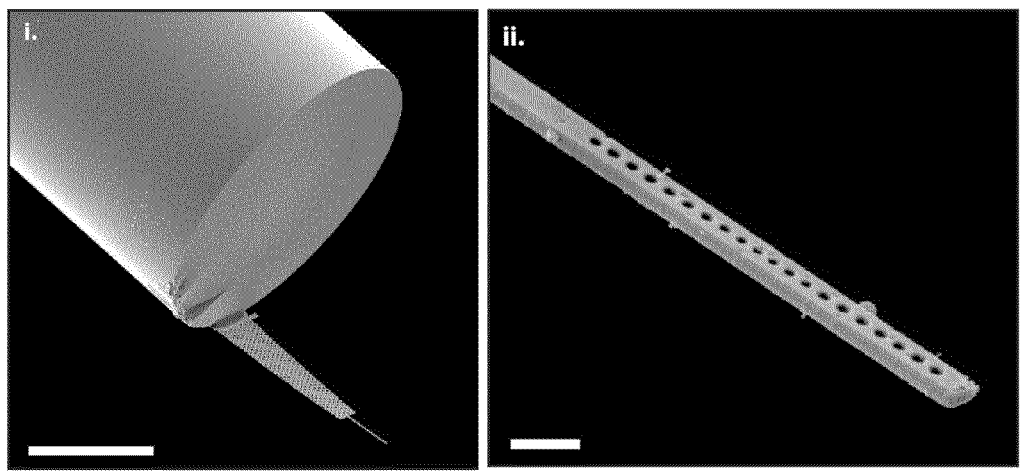

FIG. 1B shows angled scanning electron microscope (SEM) pictures of a typical fabricated device. The ripple on the fiber facet is a small fracture from the fiber cleaver. A close-up of the beam portion is shown on the right. Some light debris from the sputter coating is also visible. The striations on the side of the beam are the three wetting layers of the self-assembled quantum dots. The scale bars on the left and right are 50 μm and 1 μm respectively.

Figure 1C:
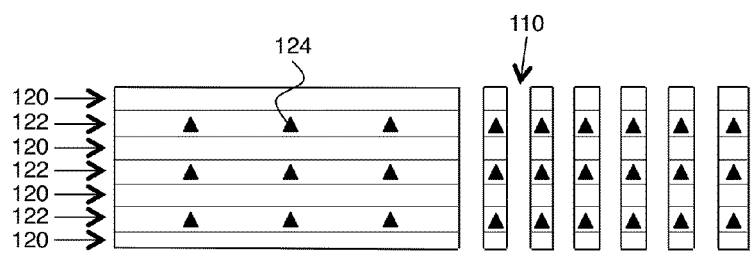

FIG. 1C is a schematic of the MBE material stack. The background material 120 is GaAs and the quantum dots (shown as triangles and one of which is referenced as 124) are InAs inside InAs wetting layers 122. The view of FIG. 1C is a cross section along the midline of the 104-106 photonic crystal structure (PCS) of FIG. 1A.

Figure 1D:
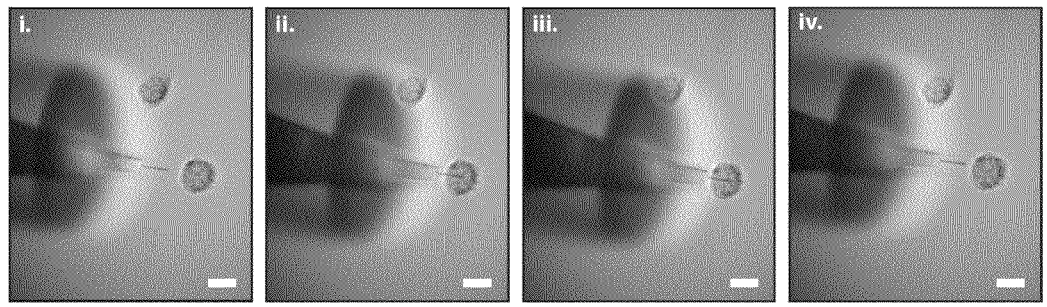

FIG. 1D shows a sequence of bright-field images of a nanocavity probe penetrating a single PC3 cell, viewed from above. The probe is first positioned outside the cell with the membrane flexed and flush against the petri dish substrate. It is then maneuvered into the side of the cell and finally retracted. The optical fiber, which is positioned higher than the membrane is seen defocused in the pictures. The scale bars for FIG. 1D are 20 μm.

Figure 1E:
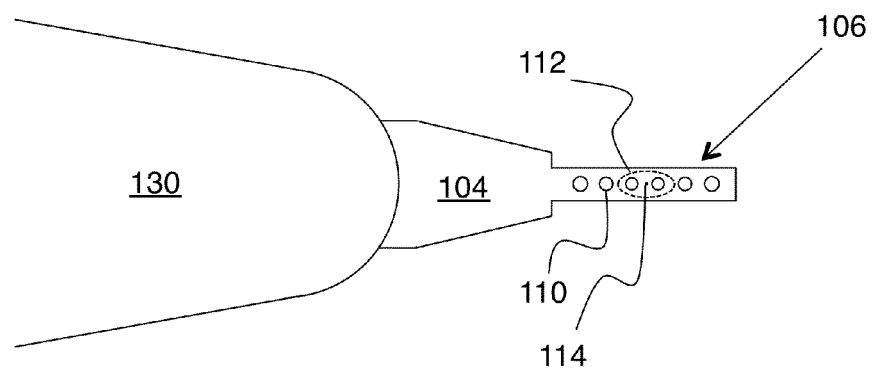
Figure 1F:
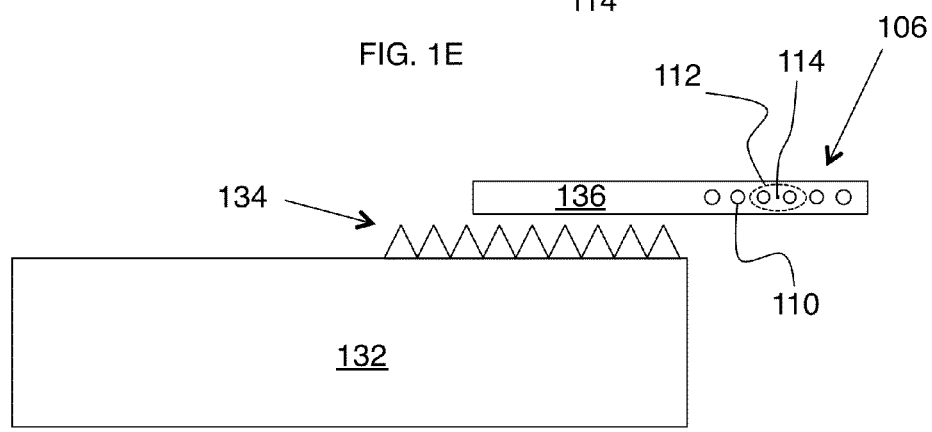

The preceding examples show coupling of the PCS structure to the end face of a fiber. Alternative fiber coupling arrangements are also possible. For example, FIG. 1E shows coupling of the PCS to the end of a tapered fiber 130. FIG. 1F shows a fiber 132 having a grating coupler 134 which optically couples to a PCS including nanobeam cavity 106 and member 136.

The overall device structure includes a semiconductor membrane epoxy bonded to the edge of a multimode optical fiber as shown in FIGS. 1A-B. Nanobeam templates were fabricated out of a thin (220 nm) membrane of gallium arsenide containing three layers of high-density indium arsenide quantum dots (QDs) (see Methods and FIG. 1C). We choose a standard five-hole taper defect nanobeam as our cavity which supports a theoretical fundamental mode Q of 95,000. The width of our beams ranged from 400-650 nm, dictated by the wavelength of the cavity modes which center around 1,300 nm (the peak gain of the QD ensemble). Templates were 200-300 µm long and narrowed down to the shown beams at the tip. Fiber tip edges were coated in epoxy and then pressed against a template handle section to rip away the entire membrane (see FIGS. 6A-C).

Once constructed, the probes can be mounted to a three-axis micropositioner for careful insertion of nanobeams into biological cells. FIG. 1D shows a top down optical micrograph sequence of a nanobeam probing a single PC3 cell, a common human prostate cancer cell line. We probe these cells by lowering the height of our device until the GaAs membrane flexes and flattens onto the petri dish surface (see section B2). This way we know that the cavity is lying flush against the substrate and will not slide over the top of a cell. As the cell gets poked by the beam, it elastically deforms upon insertion and retraction, but the overall cell morphology remains unchanged.

Figure 2A:
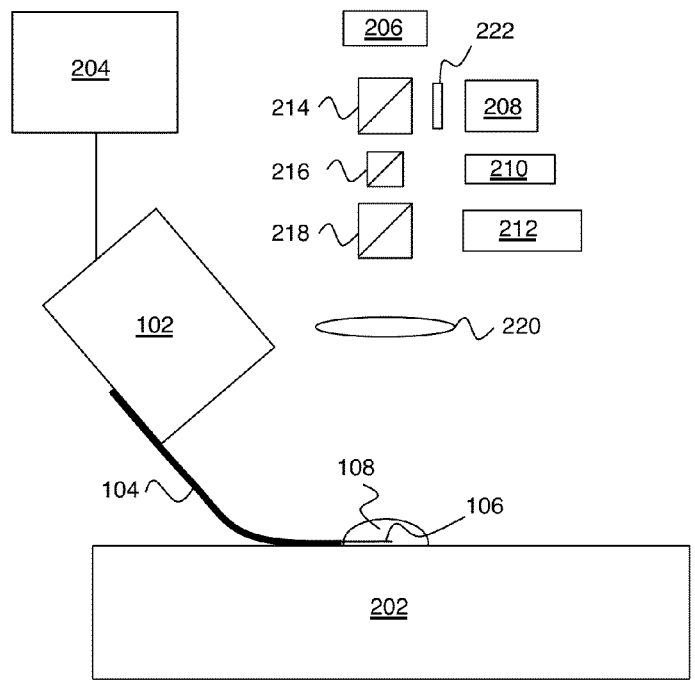
FIGS. 2A-F show optical characterization of photonic crystal cavities inside single cells.

FIGS. 2A-F show optical characterization of photonic crystal cavities inside single cells. FIG. 2A is a diagram of the optical setup used in the experiment. A three-axis micromanipulator positions the probe such that the GaAs membrane 104 flexes and rests against the substrate 202. A zoom lens tube contains beam splitters (218, 216 and 214 respectively) for laser pump (212), white light illumination (210), as well as image capture (CCD camera 206 and IR camera 208). A filter 222 is disposed in front of IR camera 208. Fiber 102 is connected to a spectrometer 204. The objective lens is referenced as 220. Not shown is the liquid level, which submerges the optical fiber 102 but does not reach the objective lens 220.

Figure 2B:
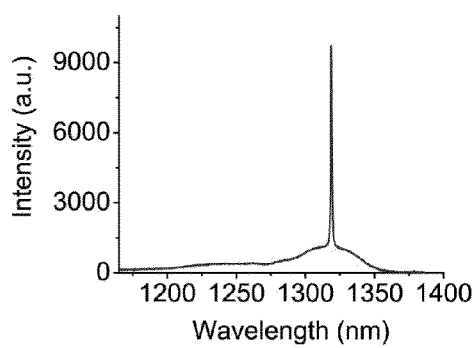

FIG. 2B is a measured photoluminescence (PL) spectrum of a single nanoprobe cavity measured in air. The QD emission uncoupled to the cavity is the small background spreading from 1,150 nm to 1,350 nm and the cavity mode is the sharp peak at 1,319 nm.

Figure 2C:
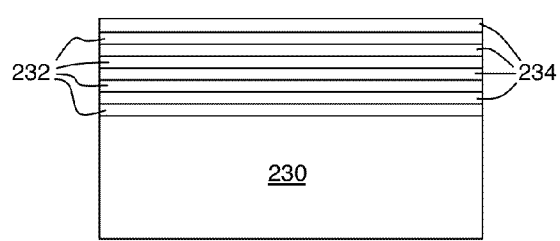

FIG. 2C is an illustration of the alumina/zirconia nanolaminate used to coat the entire device, protecting it from photo-induced oxidation. Stacks alternated between 1 nm and 2 nm per layer thicknesses, and total stack thicknesses of 7-15 nm. Here the GaAs material of the PCS is referenced as 230, the $Al_2O_3$ is referenced as 232 and the $ZrO_2$ is referenced as 234.

Figure 2D:
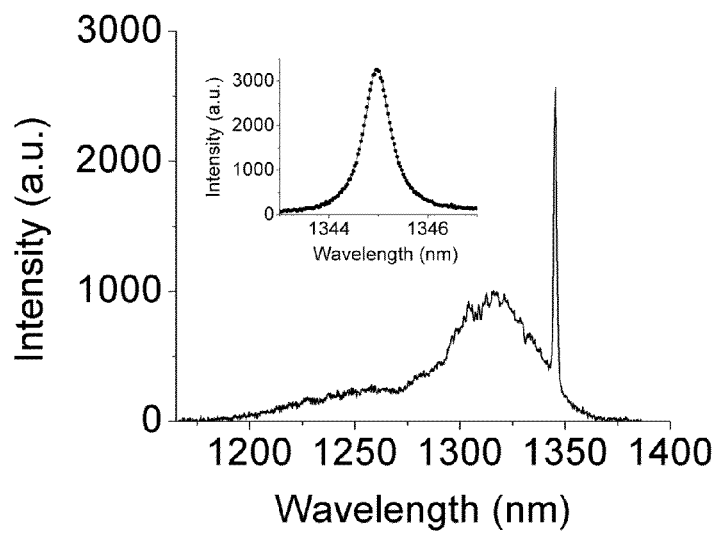

FIG. 2D is a PL spectrum of the same cavity from FIG. 2B now in a cell and its surrounding medium. There is negligible wavelength difference between the two spectra. However the collection intensity inside the cell is slightly lower, likely due to scattering from the plasma membrane. The inset of FIG. 2D shows a close-up of the cavity mode which has a Q-factor of 2,200.

Figure 2E:
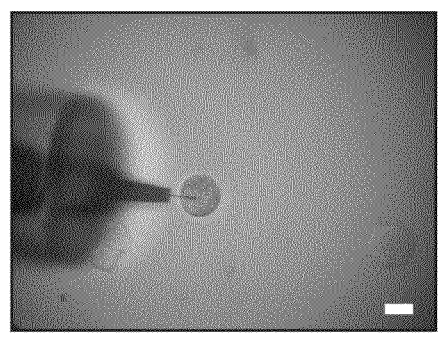

FIG. 2E is a corresponding white light image of the probe and cell for which the data of FIG. 2D were taken. The scale bar here represents 20 µm.

Figure 2F:
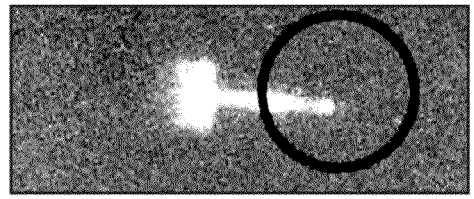

FIG. 2F is a corresponding IR image of the probe's QD emission and a circular outline of the approximate cell location.

Having demonstrated that we can insert our nanocavities into live cancer cells in culture, we next investigate their optical properties. Our testing setup is shown in FIG. 2A, and included a custom built upright zoom lens with multiple ports for laser pumping and image capture (see Methods). FIG. 2B shows a spectrum of a cavity in air prior to cell insertion, showing the fundamental mode resonance at 1,319 nm with a Q factor of 1,900, limited by fabrication imperfections (see section B1). Naïve insertion of GaAs in an aqueous solution causes destructive photo-induced oxidation, quickly removing any cavity resonance (see FIGS. 9 and 10A-C). We therefore developed a zirconia/alumina nanolaminate protective coating (FIG. 2C) for our devices which serves as a diffusion barrier to oxidants (the device in FIG. 2B has the coating already). FIG. 2D displays the nanocavity spectra when the probe is placed in a single cell, showing for the first time an active optical resonator in such a biological environment. Aside from a large redshift (26 nm) from the greater refractive index environment of the cell, we see that the cavity mode persists and actually increased in Q value to 2,000, likely due to reduced absorption by QDs at longer wavelengths. Corresponding optical and IR pictures of the cavity and cell are seen in FIGS. 2E-F.

FIGS. 3A-D show short-term cell viability results. The scale bars represent 20 µm here. FIG. 3A is a phase contrast image of two cells, one of which was poked by a nanoprobe (shown by the arrow) and one which was left untouched. FIG. 3B is a bright field image of two different cells, one which was loaded with a nanobeam and one which was left untouched. The nanobeam is the clear dark line in the upper cell. The cells look different compared to FIG. 3A because the microscope settings were changed to better visualize the cell interior. Also, the two parallel streaks are reference marks scratched into the petri dish with a metal probe to locate the treated cell. FIGS. 3C-D show green fluorescence from the calcein viability dye for the corresponding cells pictured in FIGS. 3A-B (FIG. 3C corresponds to FIG. 3A and FIG. 3D corresponds to FIG. 3B). All cells show similar levels of green fluorescence intensity indicating the viability of both poked and loaded cells. In FIG. 3D it is even possible to see the outline of the loaded beam in the cell by an absence of color.

To assess the short-term viability of our PC3 cells after probing we use a standard fluorometric assay of calcein AM and ethidium homodimer, which produces a green fluorescence for cells with live esterase activity and a red fluorescence for cells with compromised plasma membranes (see Methods). We find that 75% of cells probed by nanobeams are viable (n=20) with similar fluorescence intensities as non-probed cells (FIGS. 3C-D). The ethidium homodimer emission is very weak and uniform across all cells indicating the cell membranes were not compromised. In addition to poking cells, we have developed a method to 'load' cells with entire beam subunits which are cleaved from the original template handle (see section B4). Even under such extraordinary conditions we find that the cells can remain viable as seen in FIG. 3D.

Figure 4A:
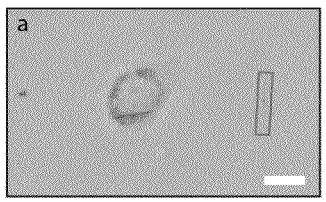
FIGS. 4A-G show nanobeam cell division and SEM (scanning electron microscope) images of loaded cells.
Figure 4B:
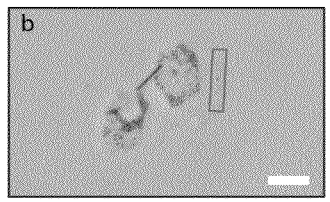
Figure 4C:
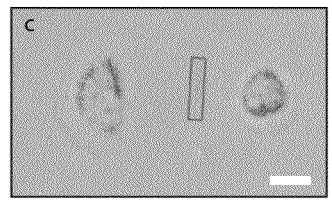
Figure 4D:
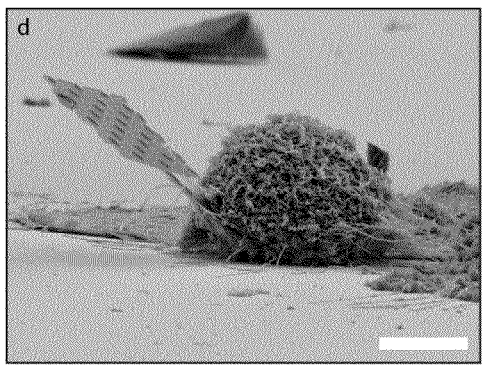
Figure 4E:
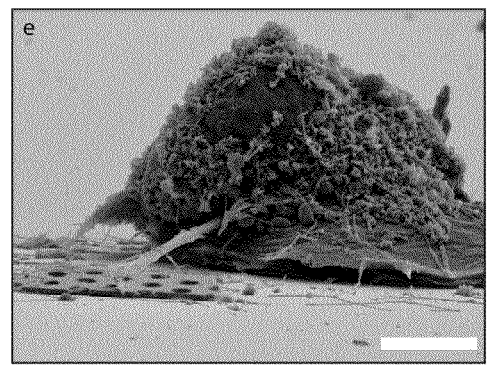
Figure 4F:
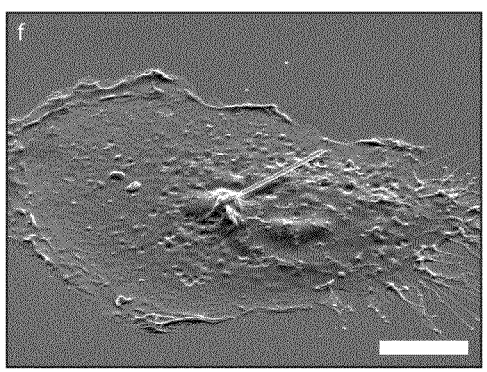
Figure 4G:
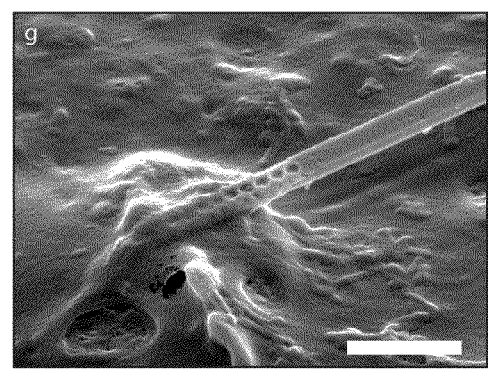

FIGS. 4A-G show nanobeam cell division and SEM images of loaded cells. FIGS. 4A-C are bright field images of a loaded cell prior (4A), during (4B), and after (4C) cell division. Images were taken 30, 42, and 46 hours after loading the cell with the nanobeam, respectively. The box indicated the position of the original scratch mark created during beam loading. This provides a reference mark for seeing how far the cells have migrated, which we observed to be up to 250 µm during the tracking period. FIG. 4D is an SEM image of a nanobeam probe including part of the handle tip lodged inside a typical cell. A few flatter cells are seen in the background. FIG. 4E is an SEM image of another cell pierced by a nanobeam with connected handle tip. FIG. 4F is an SEM image of a cell that has only a beam inserted. This cell was not critical point dried and therefore is much flatter than the cells in FIGS. 4D-E. FIG. 4G is a close-up of the entry point of the nanobeam into the cell in FIG. 4F. The holes that make up the cavity are clearly seen as they transition from fully visible outside of the cell to being hidden under the cell membrane.

The scale bars represent 20 μm (FIGS. 4A-C), 5 μm (FIGS. 4D-E), 10 μm (FIG. 4F), and 2 μm (FIG. 4G).

Inspired by the short-term survival of cells with internalized nanobeams, we performed a long-term study by constantly monitoring loaded cells over the course of one week (see section B4). We find that cells not only survive over this time period, but can perform normal cellular functions such as migration and division. FIGS. 4A-C show microscope images of a loaded cell prior to, during, and after cell division. Miraculously, the nanobeam is passed on to a daughter cell and the two subsequent cells continue to grow and divide. The implications of this result extend beyond this study and show that mesoscopic probes, photonic or otherwise, can potentially be incorporated in cells for monitoring intracellular activity over a long period of time, providing sensor feedback or sending control signals. Future investigations on how these foreign bodies perturb cell gene expression or proteomics will be necessary to identify any subtle changes in cell activity. FIGS. 4D-G show SEM pictures of fixed cells with nanobeams lodged partially in their interiors, highlighting the penetration of the beams.

FIGS. 5A-F show nanoprobe detection of Streptavidin binding. FIG. 5A is an SEM image of a modified nanoprobe that has extended 'wings' meant to wrap around the edge of the optical fiber, thus preventing sticking. Here the scale bar represents 50 μm. FIG. 5B is an illustration of the surface chemistry for protein detection. The original, nanolaminate-coated GaAs, is coated with an additional layer of silica 502 which has terminal hydroxyl groups 504. Aminosilanization with APTES yields an amine-terminated surface 506 to which biotin binds (508). Finally, Streptavidin 512 specifically binds to the surface biotin molecules (510). FIG. 5C is a finite-difference frequency domain (FDFD) simulation of the expected wavelength shift as the organic film thickness is increased. The film was modeled as a uniform layer of refractive index equal to 1.45. FIG. 5D shows spectra of a chip-bound nanobeam both before and after SA adsorption, demonstrating a clear and large redshift of the cavity peak. FIG. 5E shows that non-specific binding of a different beam cavity gives a much smaller redshift of 0.5 nm. FIG. 5F shows spectra of a nanoprobe device (as in FIG. 5A) for the same specific binding chemistry. As in FIG. 5D, the redshift is clear and large. The difference in background PL is due to slightly different focus conditions of the laser spot, however, this has no bearing on the wavelength information.

Finally, we present in vitro protein sensing results for the well-studied system of Streptavidin (SA)-biotin binding using our nanoprobes. It turns out that for repeat measurements in solution the original probe design fails because the GaAs membrane gets folded onto the fiber facet. We therefore developed a second probe design which had 'wings' that extend from the main arm and curl around the optical fiber, thus providing structural rigidity and resistance to bending (FIG. 5A). For our surface functionalization chemistry, we begin by depositing 2 nm of silica on top of our original nanolaminate using atomic layer deposition (ALD), and then proceed with the standard sequence of aminosilanization, biotinylation, and protein adsorption (FIG. 5B). From the simulation results in FIG. 5C we expect a mostly linear response of wavelength redshift with increasing coating thickness, typical of other photonic cavities. FIGS. 5D-E show the cavity signals for specific and non-specific (biotinylation was skipped) binding for nanobeam cavities attached to a chip substrate. As expected we see a large wavelength shift of 2.9 nm for the specific binding case and a much smaller 0.5 nm redshift for the non-specific binding scenario. We then apply our chemistry and sensing experiment to probe devices (as in FIG. 5A) that were individually placed in beakers and find similar results as shown in FIG. 5F. Much like the case with our planar chip cavities, we find a large (3.6 nm) redshift of the probe cavity upon Streptavidin binding. Therefore we have shown that our nanoprobes can be used to detect proteins remotely through optical readout. By adapting the chemistry and combining the method of cellular insertion it will now be possible to perform many kinds of label-free sensing experiments inside living cells.

A3) Conclusion

In conclusion, we have developed a tool which for the first time places a sophisticated photonic resonator inside an individual living cell. Our nanobeam probes are optically sound inside single cells and conversely cells with beams inside them can remain viable and even proliferate long term. We demonstrated protein sensing with our tool as an avenue towards detailed studies of label-free biomarker detection in live, single cells which could shed light on complex cellular processes such as gene expression or drug response. The range of possible applications of this merging between nanophotonics and cell biology is vast and could yield rewarding studies and understandings of fundamental cell biology.

A4) Methods

Fabrication: Wafers were grown by molecular beam epitaxy. The resultant stack included a top layer of 220 nm thick GaAs with three layers of embedded high density (300/μm$^2$) InAs QDs. Below the top GaAs membrane was a 1.5 μm layer of $Al_{0.8}Ga_{0.2}As$, which was on top of a GaAs substrate. Electron-beam lithography was used to pattern a 300 nm mask of ZEP resist after which the pattern was transferred into the GaAs membrane by dry etching with a $BCl_3/Cl_2$ electron-cyclotron resonance reactive ion etch. Structures were then undercut with hydrofluoric acid wet etching. Beams were 20 μm long with the last third of the beam patterned with the air holes that created the optical cavity. The defect cavity had an initial period a=322 nm linearly tapered down to 266 nm, with hole radius r=0.22 a. Ten holes created the cavity and an additional five holes were patterned on each side of the cavity for a total of 20 holes.

Atomic layer deposition: All depositions were performed at 200° C. in a Cambridge Nanotech Fiji ALD system. For $ZrO_2$, alternating pulses of tetrakis(dimethylamido)zirconium (TDMA-Zr) and water were used to deposit $ZrO_2$ at 0.8 A/cycle. For $Al_2O_3$, alternating pulses of trimethylaluminum (TMA) and water were used to deposit $Al_2O_3$ at 1.0 A/cycle. For $SiO_2$ a pulse of tris(dimethylamino)silane (3DMAS) was alternated with a remote $O_2$ plasma to deposit $SiO_2$ at 0.7 A/cycle. A nanolaminate of $Al_2O_3$ and $ZrO_2$ was formed by depositing either 1 nm or 2 nm of each film in sequence and repeating this process until the desired thickness was reached.

Optical Testing: Samples were tested either in a horizontal microphotoluminescence setup or in an upright custom built zoom lens setup. The horizontal setup had a free-space path for optical pumping of the sample and collection into a spectrometer. A thermoelectric cooled and stabilized laser diode (LD) operating in continuous wave mode at 830 nm was directed through a 100×0.5 numerical aperture (NA) objective lens onto the sample. PL was collected by the same objective and detected by a liquid nitrogen cooled InGaAs charge-coupled device (CCD) inside a spectrometer. The upright setup had a high magnification zoom lens (Navitar) with a laser injection port and a 20×0.4 NA objective lens. PL was collected through a 62.5 μm/125 μm core/cladding graded index fiber that was the handle to the nanoprobe. Illumination and laser pump were directed through the objective and through the cell medium onto the specimen. The nanoprobe cavity tested in air was pumped with 150 μW of laser power through the horizontal setup. The same nanoprobe cavity tested in cells and cell medium was pumped with 450 μW of laser power through the upright setup. For protein detection, we use a lower pump power of 50 μW to ensure minimal device heating. Both chip-bound nanobeams and probe nanobeams were measured using the horizontal setup both before and after the surface chemistry.

Simulation: Both FDTD (finite difference time domain) and FDFD (finite difference frequency domain) simulations were carried out on in-house custom code optimized for photonic structures.

Cell culture and handling: PC3 cells were grown in FK-12 nutrient mixture supplemented with 10% FBS and 1% penicillin/streptomycin. PC3 cells were plated at low density (several thousand cells per 10 cm gridded petri dish) and incubated at 37° C. Optics and loading experiments were performed on cells in an ambient environment for no more than 2 hours before returning samples to incubation.

Cell viability: A fluorometric assay of calcein AM and ethidium homodimer was used as per the suggested protocol (Invitrogen LIVE/DEAD). Cells were probed or loaded and the positions of those cells were documented by carving out reference marks in the petri dish using a sharp tungsten probe tip. The cells were then incubated for four hours, after which they were treated with 4 μM of calcein AM and 4 μM of ethidium homodimer. Fluorescence images were captured with a Zeiss Axiovert 25 fluorescence microscope with an X-cite mercury lamp source.

SEM imaging: Cells to be imaged were first fixed in 2% glutaraldehyde with 4% paraformaldehyde in 0.1 M Na Cacodylate buffer. We do not apply the typical lipid fixative of $OsO_4$ as we have found out that this chemical corrodes the GaAs semiconductor. Cells were then dehydrated in ethanol and either hexamethyldisilazane (HMDS) or critical point drying. Finally, cells were sputter coated with Au/Pd. Fiber probes were just coated in Au/Pd prior to imaging.

Surface chemistry: Reagents were purchased stock from Sigma Aldrich. Water used was ultrapure 18.2 MΩ reverse osmosis filtered. All glassware was cleaned in multiple washings in acetone, methanol, and water. Experimental chips were first cleaned in acetone, methanol, and water and then blow-dried in an argon stream. For the aminosilanization step, a solution of 2% 3-aminopropyltriethoxy silane (APTES) in anhydrous toluene was prepared. Samples were placed in this solution for 1.5-2 hours and then rinsed with fresh toluene, acetone, methanol, and water followed by argon blow drying. Biotinylation was performed by placing samples in a 4 mg/mL solution of N-hydroxysuccinimide-biotin ester in water for 1 hour, and then rinsed copiously in fresh water followed by argon blow drying. For Streptavidin adsorption, a solution of 100 μg/mL of Streptavidin (from *Streptomyces avidinii*) in phosphate buffered saline (PBS) was made. Samples were placed in this mixture for 40 minutes and then washed with fresh PBS and water followed by argon blow drying. Chemistry performed on fiber-mounted nanoprobes was exactly the same with the exception of there being no blow drying steps which could potentially break the probes. Fibers were manually inverted, mounted, and held in the various solutions for the described time periods.

B) Supplemental Material

B1) Device Assembly

FIGS. 6A-C provide an exemplary illustration of device assembly. Once semiconductor templates 606 have been fabricated in a membrane 608, they are aligned underneath a microscope for positioning. A droplet of epoxy 604 is coated onto the edge of a fiber 602 using a sharp electrical probe tip (FIG. 6A). The fiber is then aligned parallel to the membrane 608 using a micropositioner and then lowered into contact with the suspended membrane (FIG. 6B). After a brief pause to allow for adhesion, the fiber is retracted away, carrying the template with the beam at the tip (FIG. 6C).

Templates were fabricated as described in the Methods, and contained small tabs or bridges which connected the templates 606 to the surrounding substrate 608. The non-nanobeam portion of the template was perforated with large holes to allow for the wet etch to release the membrane. Template sizes, shapes, and tabs were optimized to prevent membrane collapse upon undercutting. Methods to tear away the membrane without breaking the structure were also optimized. It should also be noted that such large undercut structures will exhibit strong bowing effects due to built-in strain. This causes templates to warp significantly; however once the templates are torn away the strain is removed and the membranes relax. We used ITW Devcon 5 minute epoxy for the bonding process. This whole process works for silicon membranes and is likely to also work for any semiconductor or dielectric material with expected differences in material flexibility and brittleness.

Figure 7A:
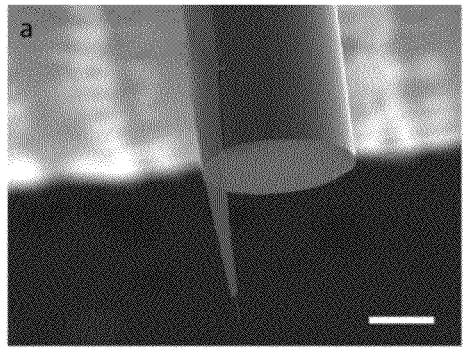
FIGS. 7A-F show SEM pictures of constructed probe devices.
Figure 7B:
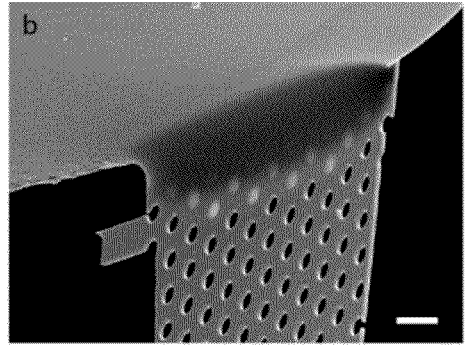
Figure 7C:
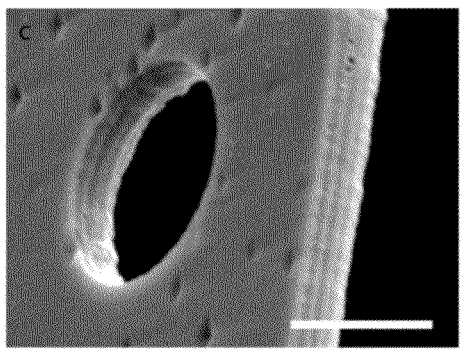
Figure 7D:
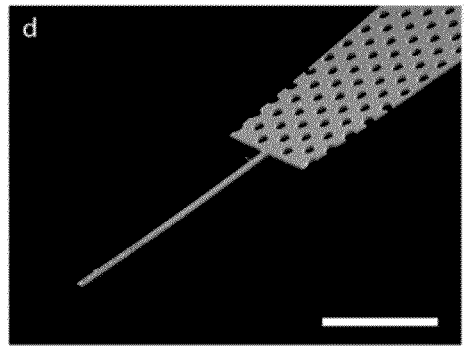
Figure 7E:
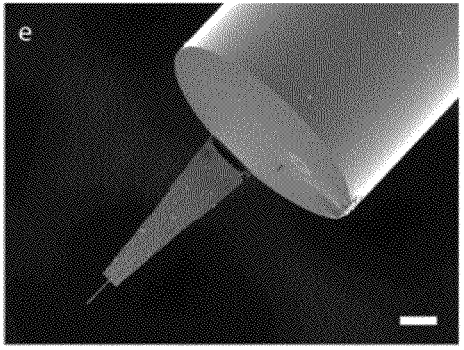
Figure 7F:
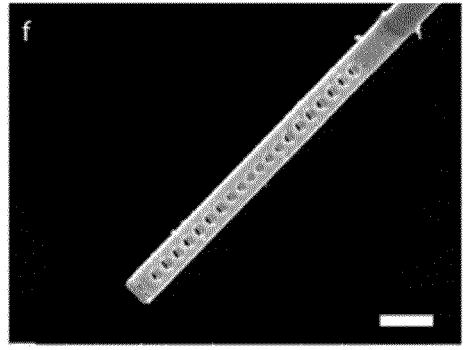

FIGS. 7A-F are SEM pictures of exemplary constructed probe devices. FIG. 7A is a view of the backside of the membrane bound to the fiber edge. The membrane lies flat along the outside of the fiber with minimal bending or undulation. FIG. 7B is a zoom-in image of the epoxy bond joint where the membrane is attached to the fiber. Also seen is a leftover template tab. FIG. 7C is a close-up of the edge of the membrane showing MBE-grown oval defects as well as the three embedded QD layers. FIG. 7D is an intermediate zoom image of the device from FIG. 1B. FIG. 7E is a second probe device imaged from a different angle, also displaying a clean construction. FIG. 7F is a zoom-in of FIG. 7E, showing the nanobeam portion with cleanly defined holes with an evident taper defect cavity. The scale bars here are 50 μm (FIG. 7A), 2 μm (FIG. 7B), 1 μm (FIG. 7C,F), 10 μm (FIG. 7D), and 20 μm (FIG. 7E).

Template structures ranged anywhere from 200-300 microns long, with a little more than half overlapping the fiber for structural support (FIG. 7A). Once the epoxy cured, the structures were very stable and would never detach in solution, a critical necessity for any kind of chemical functionalization or sensing. Even if the epoxy swelled in aqueous solution, it was never noticed since the joints are far from the nanobeam. As seen in FIG. 7C, our GaAs membrane has numerous pit-shaped defects which we believe are due to oval defects incorporated during MBE growth of the material. These pits are located everywhere and in conjunction with dry etch surface roughness limit our cavity quality factors to a few thousand. Nonetheless, for protein sensing with wavelength shifts of 2-4 nm, a quality factor of 1,000 or greater is more than sufficient for detection.

B2) Probe Insertion

Figure 8A:
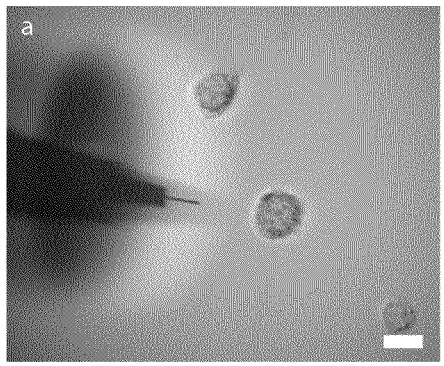
FIGS. 8A-F show details of cell probing and nanobeam flexibility.
Figure 8B:
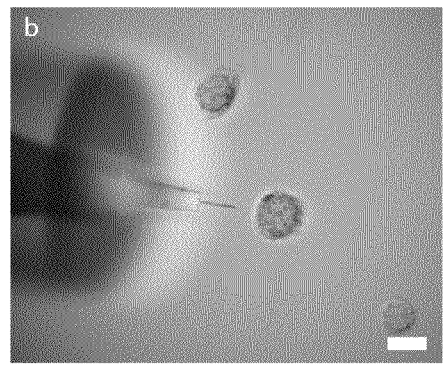
Figure 8C:
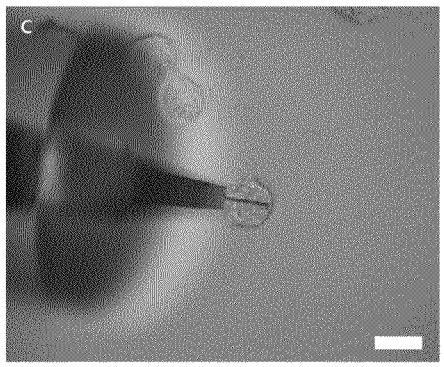
Figure 8D:
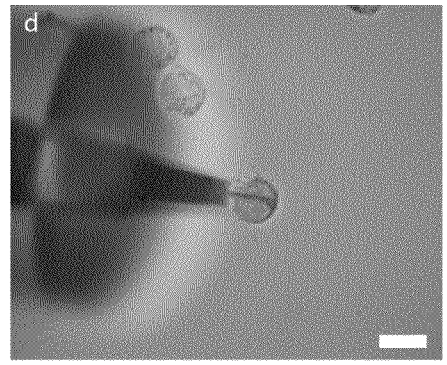
Figure 8E:
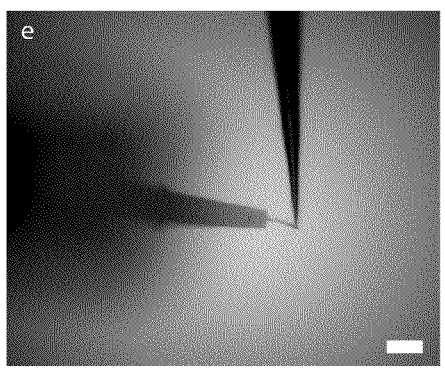
Figure 8F:
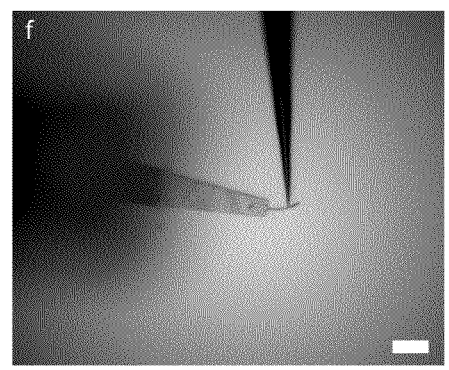

FIGS. 8A-F show details of cell probing and beam flexibility. FIG. 8A is an image of a nanoprobe hovering above the dish surface. The template is defocused and it is hard to see details of the membrane (e.g. the through holes). FIG. 8B is an image of a nanoprobe with the membrane flush against the petri dish. The template is in focus and it is possible to see the large one micron-sized holes. FIG. 8C is an image of a probe in a cell with the focus placed on the top surface of the membrane, which is known to be on the substrate. In FIG. 8D, the focus is placed on the top surface of the cell, which is several microns above the substrate surface. The beam is obscured, indicating the beam is inside the cell. FIGS. 8E-F show flexibility testing of the nanobeam by deflecting it with a 200 nm wide tip Tungsten electrical probe. The scale bars represent 20 μm for FIGS. 8A-F.

The process of probing a cell begins by bringing a mounted probe into the field of view of the microscope. Since the probe is mounted at a 30-40 degree angle from the substrate, the beam is pointing down when the device is hovering over the substrate. Therefore the membrane is defocused and it is hard to see any features (FIG. 8A). When the device is lowered, the membrane flexes and smoothly lies on the substrate surface as shown in (FIG. 8B), where now the features of the template are in focus. The probe can then be slid sideways until it punctures a cell from the side as seen in FIG. 1D.

We know that our beams go inside rather than on top of the cells by varying the focus of the image. If we focus on or near to the substrate we see that the beam and membrane are defined well (FIG. 8C); however, when we focus on the top of the cell we find that the beam is no longer clearly seen (FIG. 8D). Experimentally, there are additional cues for when the beam has successfully penetrated a cell. Upon entry, the cells typically indent until the beam is inside at which point they elastically relax back to their original shape. Upon exit, the cell edge protrudes and sticks slightly to the beam until it lets go and elastically relaxes to its original position.

The GaAs material is extremely flexible as seen in FIGS. 8E-F. For such thin membranes and for such narrow beams, the GaAs membrane can bend significantly before any breakage. Nonetheless, the material is stiff enough to penetrate the much softer cells.

B3) Material Properties

Figure 9:
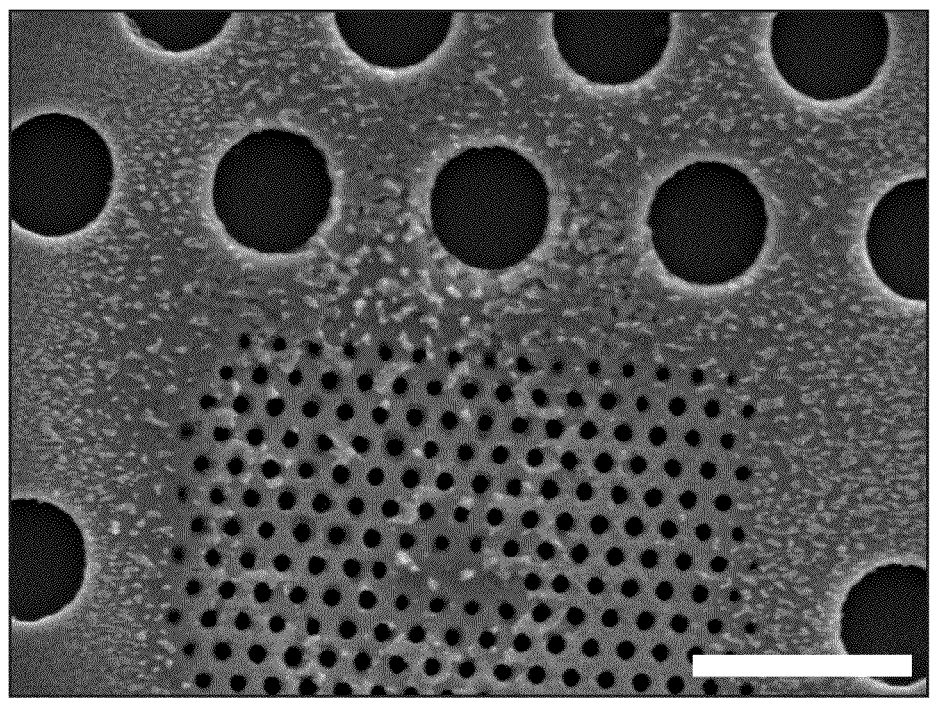
FIG. 9 shows laser induced photo-oxidation of GaAs in water.

FIG. 9 shows the effect of laser induced photo-oxidation of GaAs in water. FIG. 9 is an SEM image of a large GaAs membrane with a central two-dimensional PC cavity. The sample was submerged in water and irradiated with a continuous wave 830 nm laser with pump power less than 1 mW for ten minutes. The GaAs is clearly damaged and is flaking off in large chunks in the region where the laser pump was. Here the scale bar represents 2 μm.

Figure 10A:
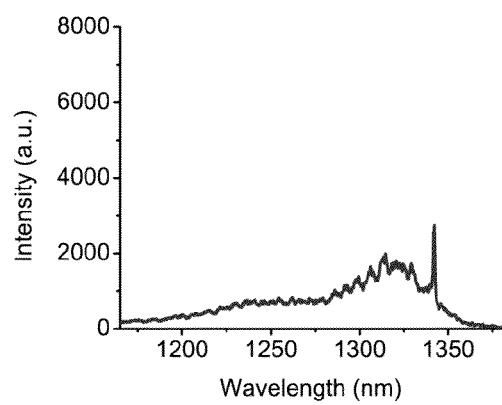
FIGS. 10A-C show effects of laser oxidation of a cavity inside a cell.
Figure 10B:
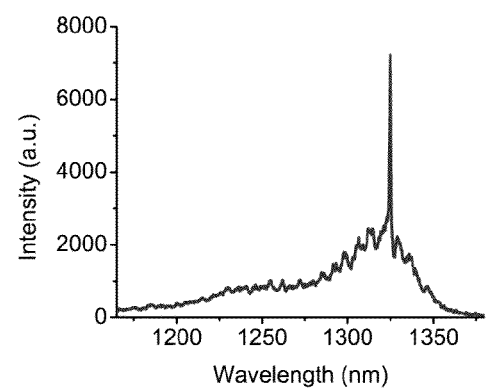
Figure 10C:
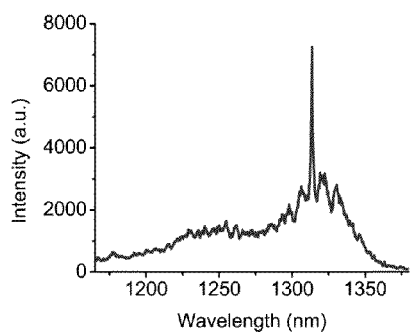
Figure 11A:
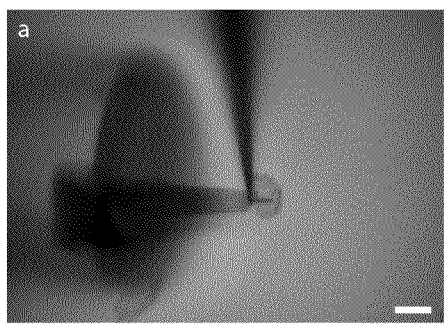
FIGS. 11A-D show a process of loading cells.
Figure 11B:
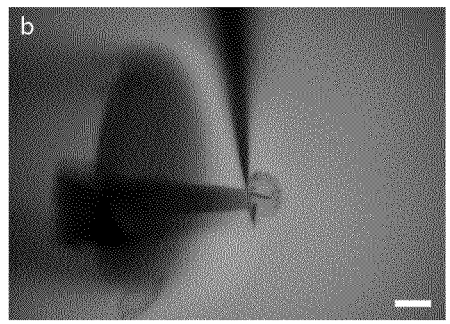
Figure 11C:
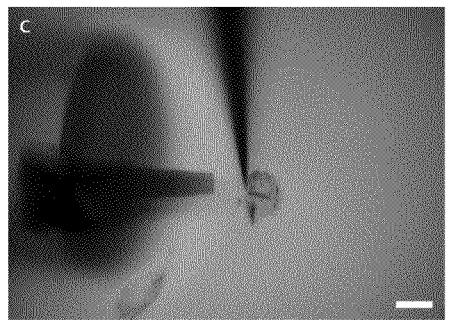
Figure 11D:

FIGS. 10A-C show a sequence of spectra for a nanoprobe that was not coated with a nanolaminate inside a cell for various time points. FIG. 10A is an initial spectrum of the cavity inside a cell. FIG. 10B is the spectrum of the cavity one minute after insertion. FIG. 10C is the spectrum of the cavity two minutes after insertion. The fringes on the background emission are from Fabry-Perot reflections off of the fiber face.

Gallium arsenide has been shown to be susceptible to laser-induced oxidation in dry air environments. This has been used in the past to fine tune PC cavity resonances by controlled amounts. Typically for this to occur the laser pump power must be in the 10 s of mW to sufficiently heat the material and catalyze the oxidation reaction. We found that when our GaAs was submerged in an aqueous environment, the threshold for observing oxidation was drastically reduced, and even pump powers as low as 100 μW could significantly oxidize cavities in minutes (FIG. 9). This causes rapid blueshifting of a cavity wavelength (as seen in FIGS. 10A-C) since the GaAs is converted into oxide which has a lower refractive index.

Since heating is unlikely in such a thermally conductive medium and with such low pump powers, it is likely that some photochemical mechanism promotes the oxidation reaction. Laser-driven oxidation in water has also been observed in the literature. We find that in other solutions such as isopropanol or acetone, which are devoid of oxidizing water molecules, no material degradation or wavelength shifting is observed, reinforcing the suggestion that oxidation is the primary factor.

In order to combat this detrimental effect, we first tried using an alumina only barrier; however we still observed rapid oxidation, in agreement with former findings of alumina not serving as a barrier to dry oxidation. We turned to the recently developed encapsulation strategy of an alumina/zirconia blend coating. This alumina/zirconia nanolaminate is superior to neat alumina because it suppresses the formation of microscopic voids and nanocrystals much more, thereby limiting permeation pathways and serving as a diffusion blocking layer. The nanolaminate coats all surfaces, including the interior of PC holes, because the plasma ALD deposition is conformal. In our application, this diffusion blocking layer prevents the reaction of water molecules with the GaAs surface and prevents laser-assisted oxidation. Coated cavities can be pumped in water solution for long periods of time with no degradation (we have tested for several hours and have seen no changes). We also note that cavities redshift 10-20 nm after the nanolaminate coating is applied depending on the layer thickness. The subsequent 26 nm redshift from FIG. 2D is due to the higher refractive index water surroundings and is in addition to the first 10-20 nm imposed by the nanolaminate.

B4) Beam Loading

FIGS. 11A-D show a process of loading cells. On FIG. 11A, a beam is inserted into a cell as normal. Then a second micromanipulator brings a sharp tungsten electrical probe tip into the field of view. On FIG. 11B, pressure is applied from the metal tip onto the joint between the nanobeam handle and the nanobeam, causing the nanobeam to snap off. The triangular mark in the picture is a scratch mark in the petri dish from the metal tip. On FIG. 11C, the fiber is retracted revealing the untethered beam. On FIG. 11D, both probes are removed with the end result of a loaded cell. Here the scale bars represent 20 μm.

The cell loading process is as depicted in FIGS. 11A-D. A tungsten metal probe tip is used to snap off the beam by applying pressure to the joint where it is connected to the rest of the template. Since the beam is about half a micron wide, this break is easy to accomplish. Nanobeams of any size can be inserted or loaded into cells. The length of the cavity on the beam is about six microns, which is determined by the number of holes we patterned (20). Therefore much smaller beams can be inserted in cells. Also, by eliminating a few hole periods or by scaling the wavelength down the cavity could be made as small as a few microns long.

Figure 12A:
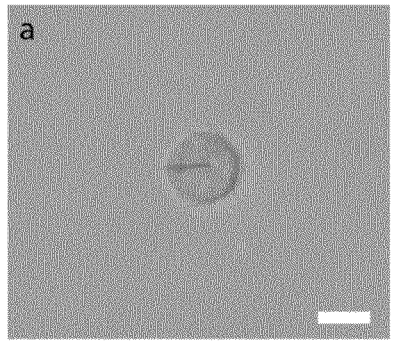
FIGS. 12A-F show tracking of loaded cells.
Figure 12B:
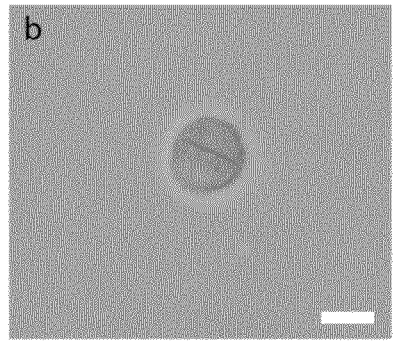
Figure 12C:
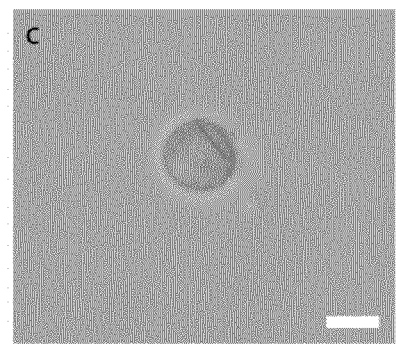
Figure 12D:
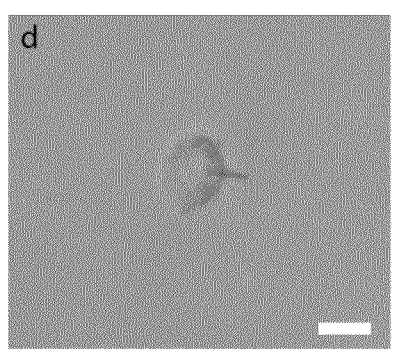
Figure 12E:
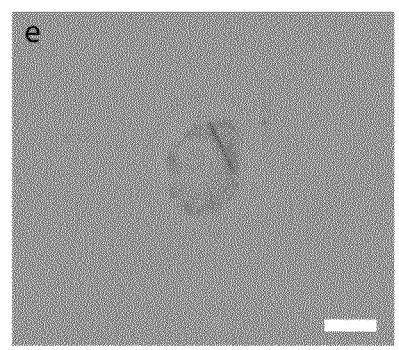
Figure 12F:
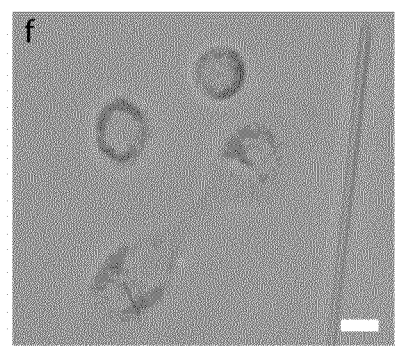

FIGS. 12A-F show tracking of loaded cells. FIGS. 12A-C show orientation tracking of a single cell with a nanobeam inside it. This cell is different from the one in FIGS. 4A-C. The nanobeam is seen to rotate at various time points. Times are at 30, 51, and 54 hours post beam insertion for FIG. 12A, FIG. 12B, and FIG. 12C, respectively. FIG. 12D shows the cell from FIG. 4A-C immediately after beam loading on day 1. The beam is only partially penetrating the cell. FIG. 12E shows the same cell three hours later. The beam has been completely internalized by the cell. FIG. 12F shows the same cell 4.5 days after initial beam loading. The cell is undergoing a second mitotic division. The cell has also migrated considerably from the initial loading location and the reference scratch mark is visible to the right. Here the scale bars represent 20 μm.

Unique to our study is the observation that cells can survive and proliferate even with large nanoprobes inside them. As seen in FIGS. 4A-C and FIG. 12F, cells can divide and produce normal new cells with one of the cells containing the beam. We find that 44% (n=9) of cells that are loaded last three days or more and some as long as eight days. The question of how normal these loaded cells are requires further investigation with gene expression profiling. It is likely that some cellular activity is modified by the presence of the large probe; however, as mentioned above the probe can be shrunk in size by a factor of 3-5 in the future. In any case, by remaining in the cell the probe can be a useful reporter of optical information for various sensing applications over a long period of time.

Figure 13A:
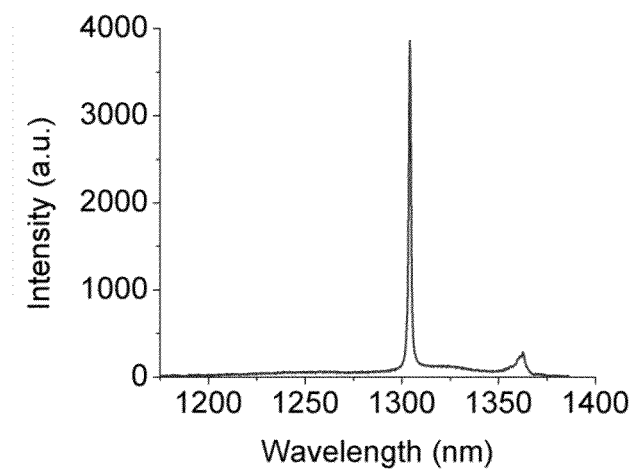
FIGS. 13A-B show photoluminescence (PL) in loaded cells.
Figure 13B:
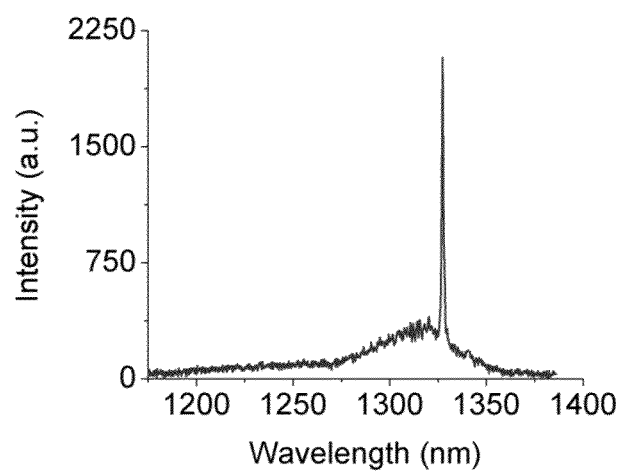

FIGS. 13A-B show PL in loaded cells. FIG. 13A is PL of a cavity probe before loading a single cell when pumped in air. FIG. 13B is PL of the same cavity probe after being broken off and loaded into a cell. We also examine the cavity properties after being loaded into a cell, no longer tethered to the original template and fiber. FIG. 13A shows a spectrum of a cavity probe prior to cellular insertion. We then proceed to break off the nanobeam cavity from the full GaAs template according to the procedure outlined above. We measure the spectrum of the internalized nanobeam four hours later using the original multimode fiber as a collection optic. The only change in the nanobeam during this period is a slight rotation due to cell movement. FIG. 13B shows this spectrum revealing once again that our cavity properties remain robust and the only major change is a redshift due to the higher refractive index water.

Figure 14A:
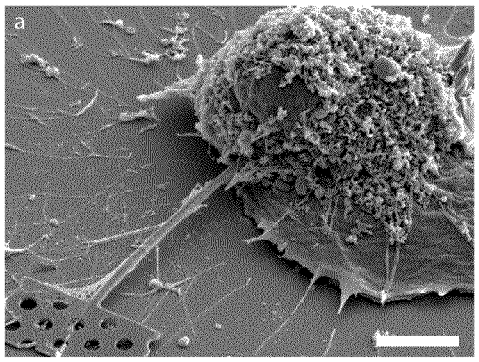
FIGS. 14A-F show SEM images of loaded and normal cells.
Figure 14B:
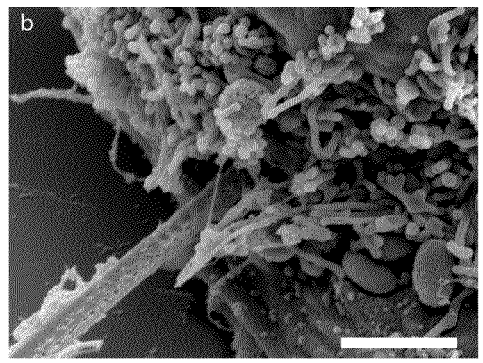
Figure 14C:
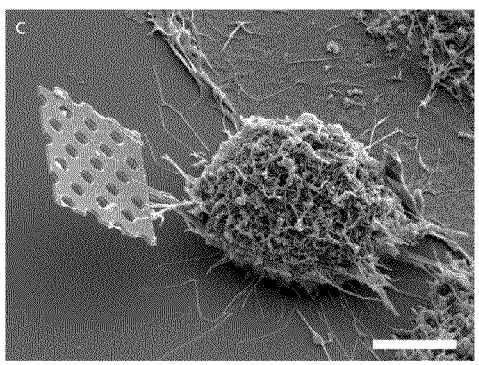
Figure 14D:
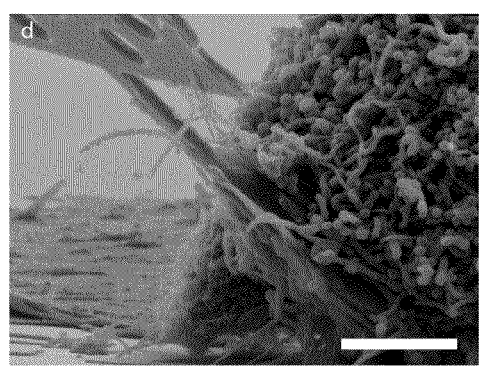
Figure 14E:
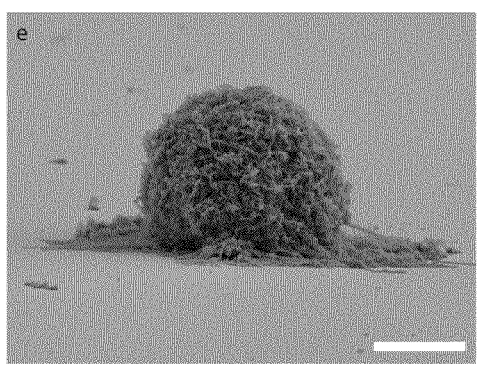
Figure 14F:
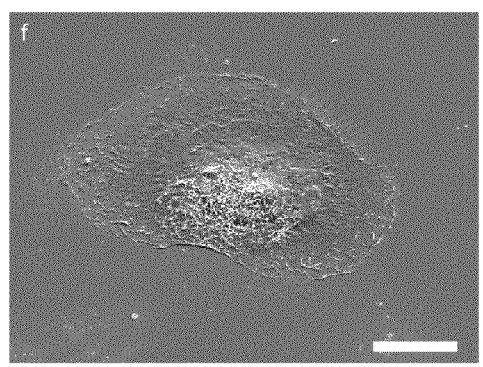

FIGS. 14A-F are SEM pictures of loaded and normal cells. FIG. 14A is a 45-degree perspective of the cell from FIG. 4E. FIG. 14B is a close-up of FIG. 14A, showing nanobeam holes disappearing into the cell. FIG. 14C is a 45-degree perspective of the cell from FIG. 4D. FIG. 14D is a close-up of FIG. 14C. FIG. 14E is a picture of a normal cell that was dehydrated by critical point drying. FIG. 14F is a picture of a normal cell that was dehydrated by HMDS. Here the scale bars represent 5 µm (FIGS. 14A,C,E), 2 µm (FIGS. 14B,D), and 20 µm (FIG. 14F).

Our loaded cells exhibit very similar morphology to non-probed cells. FIGS. 14E-F show two cells that were not probed for samples that underwent critical point drying and HMDS drying, respectively. In both cases the cells look very much like those that were loaded. As expected, the cells dried by HMDS flattened out considerably compared to those dried by critical point drying. There is significant organic debris scattered around the GaAs material and this is likely due to the fixing/dehydration process. For accurate sensing, one would want to minimize the non-specific sticking of material and this will be possible in future experiments through successive washing steps.

The invention claimed is:

1. Apparatus comprising:
   an optical fiber having an exposed fiber surface;
   a photonic crystal structure (PCS) affixed to the optical fiber and optically coupled to the optical fiber, wherein the PCS is disposed on or in proximity to the exposed fiber surface;
   wherein the PCS comprises an elongate probe member configured for biological probing; and
   wherein the elongate probe member comprises an optical resonant cavity.

2. The apparatus of claim 1, further comprising a protective coating on the PCS.

3. The apparatus of claim 2 wherein the protective coating comprises a multi-layer structure of oxides.

4. The apparatus of claim 1, wherein the PCS conforms to a curved side surface of the optical fiber, whereby structural rigidity of the PCS is improved.

5. The apparatus of claim 1, wherein the elongate probe member is configured for intracellular probing of a single biological cell.

6. The apparatus of claim 1, wherein the PCS includes an active optical element coupled to the optical resonant cavity.

7. The apparatus of claim 6, wherein the active optical element comprises an element selected from the group consisting of: quantum wells, quantum wires, quantum dots, emitters, detectors, near-field sensors, near-field emitters, photoacoustic elements, and nonlinear optical elements.

8. The apparatus of claim 1, wherein the exposed fiber surface is selected from the group consisting of: fiber end faces, tips of tapered fibers, and fiber grating couplers.

9. The apparatus of claim 1, wherein the optical resonant cavity is formed by features of the photonic crystal structure.

10. The apparatus of claim 6, wherein the active optical element provides generation, absorption and/or frequency transformation of light.

* * * * *